(12) United States Patent
Nisbet et al.

(10) Patent No.: US 8,618,322 B2
(45) Date of Patent: Dec. 31, 2013

(54) PROCESS FOR PREPARING ALKANEDIOL AND DIALKYL CARBONATE

(75) Inventors: Timothy Michael Nisbet, Amsterdam (NL); Cornelis Leonardus Maria Vrouwenvelder, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 13/498,618

(22) PCT Filed: Sep. 24, 2010

(86) PCT No.: PCT/EP2010/064153
§ 371 (c)(1),
(2), (4) Date: Mar. 28, 2012

(87) PCT Pub. No.: WO2011/039113
PCT Pub. Date: Apr. 7, 2011

(65) Prior Publication Data
US 2012/0184767 A1 Jul. 19, 2012

(30) Foreign Application Priority Data
Sep. 29, 2009 (EP) ..................... 09171674

(51) Int. Cl.
*C07C 68/08* (2006.01)
(52) U.S. Cl.
USPC ........................................ 558/277
(58) Field of Classification Search
None
See application file for complete search history.

(56) References Cited

U.S. PATENT DOCUMENTS

| 3,803,201 A | 4/1974 | Gilpin et al. ................ 3/36 |
| 4,062,884 A | 12/1977 | Romano et al. ............. 260/463 |
| 4,691,041 A | 9/1987 | Duranleau et al. ........... 558/277 |
| 5,359,118 A * | 10/1994 | Wagner et al. ............... 558/277 |
| 5,455,368 A | 10/1995 | Janisch et al. ............... 558/277 |
| 6,620,959 B1 * | 9/2003 | Buchanan et al. ........... 558/277 |
| 7,732,630 B2 * | 6/2010 | Nisbet et al. ................ 558/277 |
| 8,148,566 B2 * | 4/2012 | Tojo et al. ................... 558/277 |
| 2008/0200711 A1 * | 8/2008 | Nisbet et al. ................ 558/260 |

FOREIGN PATENT DOCUMENTS

| EP | 180387 | 10/1984 | .......... C07D 301/02 |
| EP | 274953 | 7/1988 | ............. C07C 68/06 |
| EP | 1980548 | 10/2008 | ............. C07C 27/02 |
| WO | WO03089400 | 10/2003 | ............. C07C 68/06 |
| WO | WO2004024658 | 3/2004 | ............. C07C 29/09 |
| WO | WO2008/090108 | * 7/2008 | |
| WO | WO2008090108 | 7/2008 | ............. C07C 68/06 |

OTHER PUBLICATIONS

Ullmann's Encyclopedia of Industrial Chemistry, 5$^{th}$ Ed; vol. B4, pp. 321 ff, 1992.
Knifiton, J F et al., J. Mol. Catal, vol. 67 (1991); 389 ff.

* cited by examiner

*Primary Examiner* — Jason M Nolan
*Assistant Examiner* — Po-Chih Chen

(57) ABSTRACT

The invention relates to a process for the preparation of an alkanediol and a dialkyl carbonate comprising:
reacting an alkylene carbonate and an alkanol in the presence of a transesterification catalyst to obtain a reaction mixture comprising dialkyl carbonate, unconverted alkanol, alkanediol and unconverted alkylene carbonate; and then subjecting the mixture to separation in three distillation columns.

10 Claims, 2 Drawing Sheets

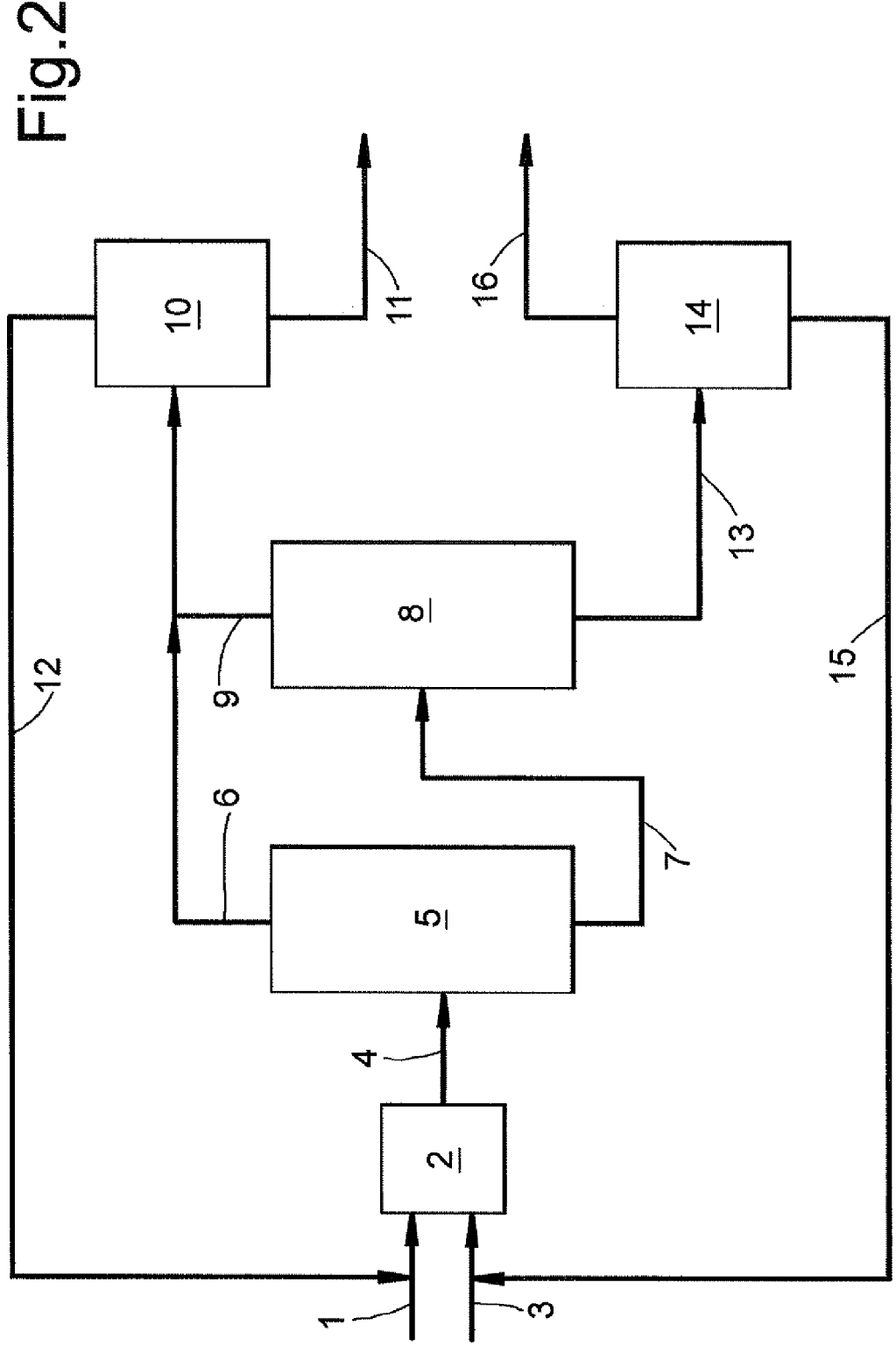

PROCESS FOR PREPARING ALKANEDIOL AND DIALKYL CARBONATE

PRIORITY CLAIM

Figure 1:
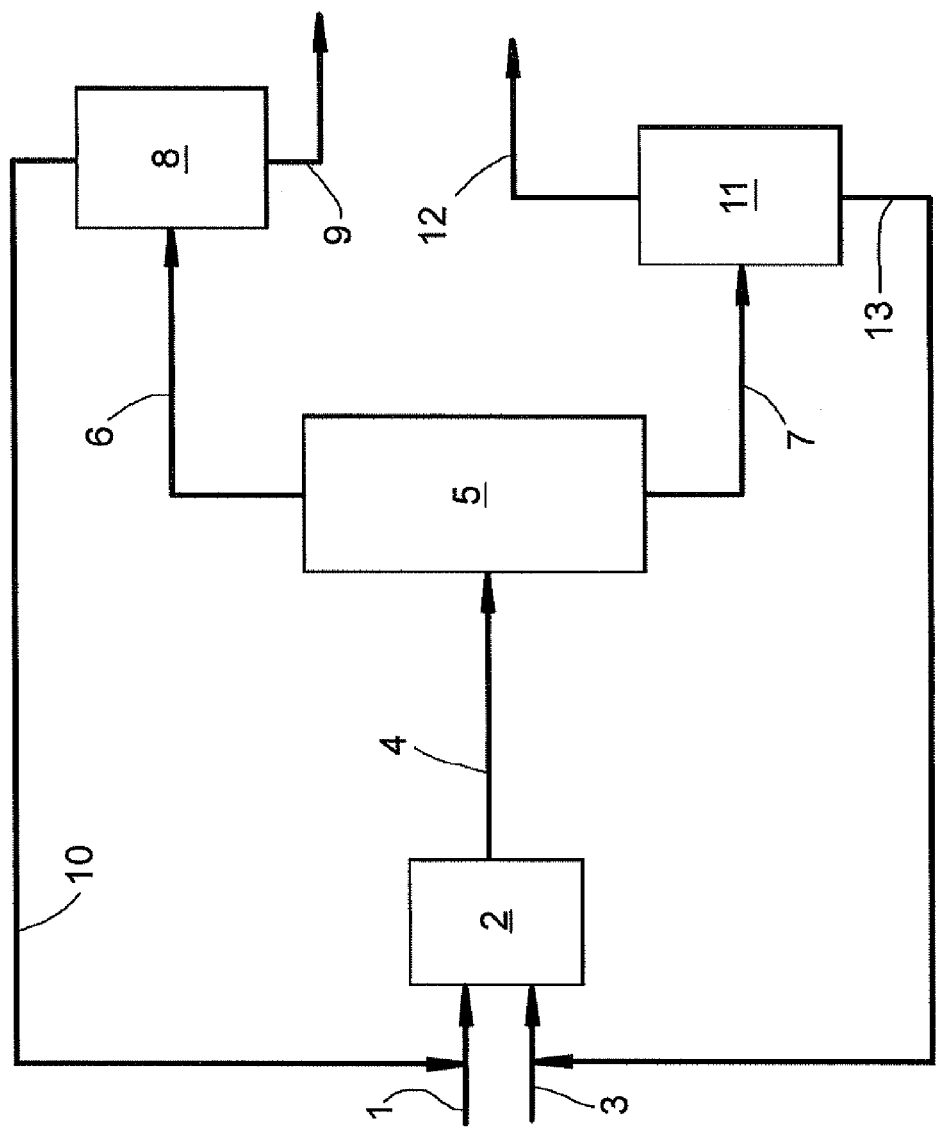

The present application claims priority from PCT/EP2010/064153, filed 24Sep. 2010, which claims priority from 09171674.6, filed 29 Sep. 2009.

The present invention relates to a process for the preparation of an alkanediol and a dialkyl carbonate from an alkylene carbonate and an alkanol.

Such transesterification processes are for example disclosed in WO2003089400 and WO2008090108. WO2008090108 discloses a process for recovering dialkyl carbonate from a reaction mixture obtained from reacting an alkylene carbonate and an alkanol. This process is shown in FIG. 1. WO2003089400 also discloses a process for recovering dialkyl carbonate from a reaction mixture obtained from reacting an alkylene carbonate and an alkanol. The latter process is similar to the one shown in FIG. 1.

In the prior art process of FIG. 1, an alkanol is passed via a line 1 into a reactor 2. Via a line 3 an alkylene carbonate is also fed into reactor 2. A product comprising a mixture of dialkyl carbonate, unconverted alkanol, alkylene glycol and unconverted alkylene carbonate is withdrawn from the reactor 2 via a line 4. Via line 4 the mixture is passed to a distillation column 5 where the product is separated into a top fraction comprising dialkyl carbonate and alkanol that is withdrawn via a line 6, and a bottom fraction comprising alkylene glycol and alkylene carbonate withdrawn via a line 7. The mixture comprising dialkyl carbonate and alkanol in line 6 is passed to a distillation column 8. Alkanol is discharged via a line 10 and recycled to reactor 2 via line 1. Dialkyl carbonate is discharged via a line 9 and recovered as product.

The bottom stream from distillation column 5 is subjected to distillation in a distillation column 11. In distillation column 11 a top product comprising alkylene glycol is recovered via line 12. The bottom product of distillation column 11 withdrawn via line 13 comprises alkylene carbonate, which is (partly) recycled to reactor 2 via line 3.

The object of the present invention is to find a process for the preparation of an alkanediol and a dialkyl carbonate by reacting an alkylene carbonate and an alkanol, wherein after the reaction the dialkyl carbonate can be recovered in a most energy efficient way.

Surprisingly it was found that such energy efficient recovery of dialkyl carbonate can be achieved by adding an additional distillation column directly downstream of the transesterification reactor, as compared to the set-up shown in FIG. 1. The set-up for recovering dialkyl carbonate according to the present invention is shown in FIG. 2.

Accordingly, the present invention relates to a process for the preparation of an alkanediol and a dialkyl carbonate comprising:
(a) reacting an alkylene carbonate and an alkanol in the presence of a transesterification catalyst to obtain a reaction mixture comprising dialkyl carbonate, unconverted alkanol, alkanediol and unconverted alkylene carbonate;
(b) subjecting the reaction mixture to distillation in a first distillation column to obtain a top stream comprising dialkyl carbonate and alkanol and a bottom stream comprising dialkyl carbonate, alkanol, alkanediol and alkylene carbonate;
(c) subjecting the bottom stream from the first distillation column to distillation in a second distillation column to obtain a top stream comprising dialkyl carbonate and alkanol and a bottom stream comprising alkanediol and alkylene carbonate;
(d) recovering alkanediol from the bottom stream from the second distillation column; and
(e) subjecting the top streams from the first and second distillation columns to distillation in a third distillation column to obtain a top stream comprising alkanol and a bottom stream comprising dialkyl carbonate.

The present invention advantageously results in less stringent energy requirements for separating the dialkyl carbonate from the reaction mixture, as is shown in the Examples below.

Step (a) of the present process may be carried out in a reactive distillation column, as described in U.S. Pat. No. 5,359,118. This would entail that the reaction is carried out counter-currently. The distillation column may contain trays with bubble caps, sieve trays, or Raschig rings. The skilled person will realise that several types of packings of transesterification catalyst and several tray configurations will be possible. Suitable columns have been described in, e.g., Ullmann's Encyclopedia of Industrial Chemistry, 5$^{th}$ ed. Vol. B4, pp 321 ff, 1992.

The alkylene carbonate will generally have a higher boiling point than the alkanol. In the case of ethylene and propylene carbonate the atmospheric boiling points are above 240° C. Therefore, in general, the alkylene carbonate will be fed at the upper part of a reactive distillation column and alkanol will be fed at the lower part of such column. The alkylene carbonate will flow downwardly, and the alkanol will flow upwardly.

Preferably, step (a) of the present process is conducted in a co-current manner. A suitable way to operate is to carry out the reaction in a trickle-flow manner wherein the reactants part in vapour phase and part in liquid phase drip down over a heterogeneous catalyst. A more preferred way to operate step (a) of the process of the present invention is in a reactor with only liquids. A suitable reaction zone of this type is a pipe-type reaction zone wherein the reaction is conducted in a plug flow manner. For example, step (a) of the present process may be carried out in one plug flow reactor or in a series of two or more plug flow reactors. This will enable the reaction to approach equilibrium.

A further possibility is to conduct step (a) of the process of the present invention in a continuously stirred tank reactor (CSTR). In the latter case the effluent from the CSTR is preferably subjected to a post-reaction in a plug flow reactor so that the reaction can approach equilibrium.

In step (b) of the present process, the reaction mixture comprising dialkyl carbonate, unconverted alkanol, alkanediol and unconverted alkylene carbonate from step (a) is subjected to distillation in a first distillation column to obtain a top stream comprising dialkyl carbonate and alkanol and a bottom stream comprising dialkyl carbonate, alkanol, alkanediol and alkylene carbonate.

In accordance with the present description, a top stream or product from a distillation column comes from the top or from the upper part of the distillation column. Likewise, a bottom stream or product comes from the bottom or from the lower part of the distillation column. This implies that a top stream may be discharged from either the highest tray or from a tray positioned below the highest tray, and that a bottom stream may be discharged from either the lowest tray or from a tray positioned above the lowest tray.

Preferably, the pressure at the top of the first distillation column is of from 0.5 to 10 bar, more preferably 1 to 5 bar. The pressure at the top of a distillation column is the lowest pressure within said column. Further, preferably, the temperature at the bottom of the first distillation column is of from 100 to 200° C., more preferably 125 to 175° C. The temperature at the bottom of a distillation column is the highest temperature within said column.

Both the top stream and bottom stream from the first distillation column may comprise considerable amounts of dialkyl carbonate and alkanol.

The amount of dialkyl carbonate that leaves the first distillation column via the top stream is preferably of from 40 to 80 wt. %, more preferably 50 to 70 wt. %, based on total amount of dialkyl carbonate present in the first distillation column. The amount of dialkyl carbonate that leaves the first distillation column via the bottom stream is preferably of from 20 to 60 wt. %, more preferably 30 to 50 wt. %, based on total amount of dialkyl carbonate present in the first distillation column.

The amount of alkanol that leaves the first distillation column via the top stream is preferably of from 60 to 99 wt. %, more preferably 80 to 95 wt. %, based on total amount of alkanol present in the first distillation column. The amount of alkanol that leaves the first distillation column via the bottom stream is preferably of from 1 to 40 wt. %, more preferably 5 to 20 wt. %, based on total amount of alkanol present in the first distillation column.

In step (c) of the present process, the bottom stream from the first distillation column comprising dialkyl carbonate, alkanol, alkanediol and alkylene carbonate is subjected to distillation in a second distillation column to obtain a top stream comprising dialkyl carbonate and alkanol and a bottom stream comprising alkanediol and alkylene carbonate.

Preferably, the pressure at the top of the second distillation column is of from 10 mbar to 3 bar, more preferably 50 mbar to 1 bar. Specifically, the pressure at the top of the second distillation column is lower than the pressure at the top of the first distillation column, and is of from 50 to 500 mbar, more preferably 70 to 300 mbar. Further, preferably, the temperature at the bottom of the second distillation column is of from 100 to 200° C., more preferably 125 to 175° C.

In step (e) of the present process, the top streams from the first and second distillation columns comprising dialkyl carbonate and alkanol are subjected to distillation in a third distillation column to obtain a top stream comprising alkanol and a bottom stream comprising dialkyl carbonate.

Preferably, the pressure at the top of the third distillation column is lower than the pressure at the top of the first distillation column, and is of from 0.1 to 5 bar, more preferably 0.5 to 4 bar. Further, preferably, the top stream from the first distillation column is sent as a vapour stream to the third distillation column. Further, preferably, the temperature at the bottom of the third distillation column is of from 100 to 200° C., more preferably 125 to 175° C.

When the dialkyl carbonate and the alkanol form an azeotrope or have close boiling points it may be beneficial to use extractive distillation in said third distillation column, using an extractant to facilitate the separation between the dialkyl carbonate and the alkanol. The extractant can be selected from many compounds, in particular alcohols such as phenol or ethers such as anisole. However, it is preferred to employ an alkylene carbonate as extractant. It is most advantageous to obtain the separation in the presence of the alkylene carbonate that is being used as starting material.

The top stream from the third distillation column comprising unconverted alkanol may be recycled to transesterification step (a).

The bottom stream from the third distillation column comprising dialkyl carbonate may be subjected to a further purification. This further purification may comprise an ion-exchange step, as described in U.S. Pat. No. 5,455,368. Alternatively, said bottom stream from the third distillation column may be subjected to distillation in another distillation column to obtain a top stream comprising dialkyl carbonate and a bottom stream comprising compounds having a higher boiling point than dialkyl carbonate.

In step (d) of the present process, alkanediol is recovered from the bottom stream from the second distillation column comprising alkanediol and alkylene carbonate. A process for recovery of alkanediol from a stream comprising alkanediol and unconverted alkylene carbonate is disclosed in abovementioned WO2008090108, which is herein incorporated by reference. Unconverted alkylene carbonate separated from alkanediol may be recycled to transesterification step (a).

The process of the present invention is preferably carried out continuously.

The process of the present invention includes in step (a) the transesterification of an alkylene carbonate with an alkanol. The starting materials of the transesterification are preferably selected from $C_2$-$C_6$ alkylene carbonate and $C_1$-$C_4$ alkanols. More preferably the starting materials are ethylene carbonate or propylene carbonate and methanol, ethanol or isopropanol, most preferably ethanol.

In step (a) of the present process, the presence of a transesterification catalyst is required. Suitable homogeneous transesterification catalysts have been described in U.S. Pat. No. 5,359,118 and include hydrides, oxides, hydroxides, alcoholates, amides, or salts of alkali metals, i.e., lithium, sodium, potassium, rubidium and cesium. Preferred catalysts are hydroxides or alcoholates of potassium or sodium. It is advantageous to use the alcoholate of the alkanol that is being used as feedstock.

Other suitable catalysts are alkali metal salts, such as acetates, propionates, butyrates, or carbonates. Further suitable catalysts are described in U.S. Pat. No. 5,359,118 and the references mentioned therein, such as EP274953, U.S. Pat. No. 3,803,201, EP1082, and EP180387.

As indicated in U.S. Pat. No. 5,359,118, it is also possible to employ heterogeneous catalysts. In the current process, the use of heterogeneous transesterification catalysts in step (a) is preferred. Suitable heterogeneous catalysts include ion exchange resins that contain functional groups. Suitable functional groups include tertiary amine groups and quaternary ammonium groups, and also sulphonic acid and carboxylic acid groups. Further suitable catalysts include alkali and alkaline earth silicates. Suitable catalysts have been disclosed in U.S. Pat. No. 4,062,884 and U.S. Pat. No. 4,691,041. Preferably, the heterogeneous catalyst is selected from ion exchange resins comprising a polystyrene matrix and tertiary amine functional groups. An example is Amberlyst A-21 (ex Rohm & Haas) comprising a polystyrene matrix to which N,N-dimethylamine groups have been attached. Eight classes of transesterification catalysts, including ion exchange resins with tertiary amine and quaternary ammonium groups, are disclosed in J F Knifton et al., J. Mol. Catal, 67 (1991) 389ff. Further suitable transesterification catalysts are zinc supported catalysts such as those as disclosed in WO2004024658. Preferably, such zinc supported catalyst comprises a support material which is selected from the group comprising $SiO_2$, $Al_2O_3$, MgO, $TiO_2$, $ZrO_2$, $Cr_2O_3$, C and mixtures thereof.

The transesterification conditions in step (a) of the present process include a temperature of from 10 to 200° C., and a pressure of from 0.5 to 50 bar ($5\times10^4$ to $5\times10^6$ $N/m^2$). Preferably, especially in co-current operation, said pressure ranges from 1 to 20 bar, more preferably 1.5 to 20 bar, most preferably 2 to 15 bar, and said temperature ranges from 30 to 200° C., more preferably 40 to 170° C., most preferably 50 to 150° C.

Further, preferably an excess of the alkanol over the alkylene carbonate is used in step (a) of the present process. The molar ratio of alkanol to alkylene carbonate in said step (a) is suitably of from 1.01:1 to 25:1, preferably of from 2:1 to 20:1, more preferably of from 4:1 to 17:1, most preferably from 5:1 to 15:1. The amount of catalyst in step (a) of the present process can be of from 0.1 to 5.0% wt based on alkylene carbonate (i.e. total alkylene carbonate as fed to step (a) of the present process), preferably of from 0.2 to 2% wt. The weight hourly space velocity in step (a) of the present process may suitably range of from 0.1 to 100 kg/kg.hr.

The process of the present invention can be employed for a variety of feedstocks. The process is excellently suited for the preparation of monoethylene glycol (1,2-ethanediol), monopropylene glycol (1,2-propanediol), dimethyl carbonate and/or diethyl carbonate and/or diisopropyl carbonate. The process is most advantageously used for the production of monoethylene glycol or propylene glycol and diethyl carbonate from ethylene carbonate or propylene carbonate and ethanol.

In FIG. 2 a flow scheme for the process according to the present invention is shown. Although the process will be described for ethanol as a suitable alcohol and ethylene carbonate as the alkylene carbonate the skilled person will understand that other alkanols and alkylene carbonates can be similarly used.

Ethanol is passed via a line 1 into a reactor 2. Reactor 2 can suitably be a continuously stirred tank reactor. Via a line 3 ethylene carbonate is also fed into reactor 2. A transesterification catalyst is present in reactor 2, which catalyst may be fed continuously to said reactor. The catalyst may be mixed with the reactants in line 1 or line 3 or fed to the reactor 2 via a separate line (not shown).

Via a line 4, the reaction mixture from reactor 2, comprising diethyl carbonate, unconverted ethanol, monoethylene glycol and unconverted ethylene carbonate, is fed into a first distillation column 5. In distillation column 5, said mixture is separated into a top fraction comprising diethyl carbonate and ethanol that is withdrawn via a line 6, and a bottom fraction comprising diethyl carbonate, ethanol, monoethylene glycol and ethylene carbonate that is withdrawn via a line 7.

The bottom stream in line 7 is subjected to distillation in a second distillation column 8. In distillation column 8 a top product comprising diethyl carbonate and ethanol is withdrawn via line 9.

The top streams from distillation columns 5 and 8 are combined and sent to a third distillation column 10, where separation into ethanol and diethyl carbonate is performed. The diethyl carbonate is discharged via a line 11 and recovered as product, optionally after further purification. Ethanol is recovered via a line 12 and via line 1 recycled to reactor 2.

Further, in distillation column 8 a bottom stream comprising monoethylene glycol and ethylene carbonate is withdrawn via line 13, and sent to a distillation column 14. The bottom product of distillation column 14 withdrawn via line 15 comprises ethylene carbonate. Said ethylene carbonate in line 15 is recycled, optionally after further purification, to reactor 2 via line 3. Monoethylene glycol is recovered from the top product of distillation column 14 which is withdrawn via a line 16. Since said top product may be slightly contaminated with some ethylene carbonate further purification may be considered.

The invention is further illustrated by the following Examples.

EXAMPLE AND COMPARATIVE EXAMPLE

In the Example exemplifying the invention, the set-up as shown in FIG. 2 is used to produce diethyl carbonate (DEC) and monoethylene glycol (MEG) from ethylene carbonate (eC) and ethanol in reactor 2, and to separate DEC and MEG from the reaction mixture in distillation columns 5, 8, 10 and 14 as further described below.

In the Comparative Example exemplifying a prior art process as for example described in above-mentioned WO2003089400 and WO2008090108, the set-up as shown in FIG. 1 is used to produce DEC and MEG from eC and EtOH in reactor 2, and to separate DEC and MEG from the reaction mixture in distillation columns 5, 8 and 11 as further described below.

In the Example and the Comparative Example, EtOH is continuously passed via line 1 into reactor 2 containing catalyst. Via line 3 eC is also continuously fed into reactor 2. Within reactor 2, the temperature is 130-140° C. and the pressure is 12 bar.

A mixture consisting of DEC (13 wt. %), unconverted EtOH (56 wt. %), MEG (7 wt. %), unconverted eC (13 wt. %) and compounds having a higher molecular weight than MEG (11 wt. %) is withdrawn from reactor 2 via line 4. Via line 4 the mixture is passed to distillation column 5 where it is separated into a top fraction that is withdrawn via line 6 and a bottom fraction that is withdrawn via line 7.

In the Comparative Example, the stream in line 6 is passed to distillation column 8 (as shown in FIG. 1). EtOH is discharged via line 10 and recycled to reactor 2 via line 1. DEC is discharged via line 9 and recovered as product. Further, in the Comparative Example, the stream in line 7 is passed to distillation column 11 (as shown in FIG. 1). eC is discharged via line 13 and recycled to reactor 2 via line 3. MEG is discharged via line 12 and recovered as product.

In Table 1 below, a few characteristics for columns 5, 8 and 11 used in the Comparative Example are mentioned.

TABLE 1

| | Comparative Example | | | |
|---|---|---|---|---|
| Column no. in FIG. 1 | Total number of theoretical stages | Stage at which feed is let in (*) | Column diameter (m) | Reflux ratio (R/D) |
| Column 5 | 15 | 5 | 3.5 | 0.03 |
| Column 8 | 20 | 16 | 2.9 | 1.04 |
| Column 11 | 30 | 26 | 1.9 | 1.21 |

(*) The condenser of the column is represented by stage no. 1.

In Table 2 below, the following parameters are provided for the streams from the Comparative Example as present in lines 1, 3, 4, 6, 7, 9, 10, 12 and 13 as indicated in FIG. 1: temperature, pressure, total mass flow and the mass flow (MF) per component of the stream. All streams in the Comparative Example are liquid.

TABLE 2

Comparative Example

| | line | | | | | | | | |
|---|---|---|---|---|---|---|---|---|---|
| | 1 | 3 | 4 | 6 | 7 | 9 | 10 | 12 | 13 |
| T | 25.6 | 125.6 | 125.0 | 30 | 155.4 | 126.7 | 77.1 | 117 | 153.4 |
| P | 12 | 12 | 12 | 0.12 | 0.16 | 1.05 | 1 | 0.05 | 0.07 |
| TMF | 4.162 | 4.709 | 45.187 | 32.487 | 12.237 | 4.825 | 27.662 | 2.773 | 9.464 |
| MF eC | 0 | 4.692 | 6.014 | 0 | 8.151 | 0 | 0 | 0.267 | 7.884 |
| MF EtOH | 4.162 | 0 | 26.212 | 26.971 | 0 | 0.002 | 26.969 | 0 | 0 |
| MF MEG | 0 | 0.009 | 2.572 | 0 | 2.512 | 0 | 0 | 2.506 | 0.006 |
| MF DEC | 0 | 0 | 5.559 | 5.513 | 0 | 4.823 | 0.69 | 0 | 0 |
| MF heavies | 0 | 0.007 | 4.767 | 0 | 1.573 | 0 | 0 | 0 | 1.573 |

Explanation:
T = temperature (° C.);
P = pressure (bar),
TMF = total mass flow (ton/h);
MF = mass flow (ton/h);
eC = ethylene carbonate;
EtOH = ethanol;
MEG = monoethylene glycol;
DEC = diethyl carbonate;
heavies = compounds having a higher molecular weight than MEG.
Except for the streams in lines 1 and 3, the above data relate to the streams at a point in the lines where the streams just leave the reactor or column in question.

In the Example, the stream in line 7 is passed to distillation column 8 (as shown in FIG. 2). The top streams from distillation columns 5 and 8, in lines 6 and 9, respectively, are combined and sent to distillation column 10. EtOH is discharged via line 12 and recycled to reactor 2 via line 1. DEC is discharged via line 11 and recovered as product. Further, in the Example, the bottom stream from distillation column 8, in line 13, is passed to distillation column 14 (as shown in FIG. 2). eC is discharged via line 15 and recycled to reactor 2 via line 3. MEG is discharged via line 16 and recovered as product.

In Table 3 below, a few characteristics for columns 5, 8, 10 and 14 used in the Example are mentioned.

TABLE 3

Example

| Column no. in FIG. 2 | Total number of theoretical stages | Stage at which feed is let in (*) | Column diameter (m) | Reflux ratio (R/D) |
|---|---|---|---|---|
| Column 5 | 7 | 7 | 1.7 | 0.10 |
| Column 8 | 15 | 5 | 1.6 | 0.23 |

TABLE 3-continued

Example

| Column no. in FIG. 2 | Total number of theoretical stages | Stage at which feed is let in (*) | Column diameter (m) | Reflux ratio (R/D) |
|---|---|---|---|---|
| Column 10 | 20 | 16 | 2.2 | 0.58 |
| Column 14 | 35 | 29 | 1.7 | 0.88 |

(*) The condenser of the column is represented by stage no. 1.

In Table 4 below, the following parameters are provided for the streams from the Example as present in lines 1, 3, 4, 6, 7, 9, 11, 12, 13, 15 and 16 as indicated in FIG. 2: temperature, pressure, total mass flow and the mass flow (MF) per component of the stream. For an explanation of Table 4 reference is made to the explanation given below Table 2. All streams in the Example are liquid, except for the stream in line 6 which stream is vaporous.

TABLE 4

Example

| | Line | | | | | | | | | | |
|---|---|---|---|---|---|---|---|---|---|---|---|
| | 1 | 3 | 4 | 6 | 7 | 9 | 11 | 12 | 13 | 15 | 16 |
| T | 25.6 | 125.6 | 122.9 | 111.1 | 150 | 33.1 | 150.3 | 95 | 155.1 | 153.4 | 113.9 |
| P | 12 | 12 | 12 | 3 | 3.05 | 0.12 | 2.05 | 2 | 0.16 | 0.07 | 0.05 |
| TMF | 3.812 | 4.709 | 45.92 | 27.646 | 18.274 | 6.046 | 4.897 | 27.659 | 12.227 | 9.477 | 2.751 |
| MF eC | 0 | 4.692 | 6.017 | 0 | 6.017 | 0 | 0 | 0 | 8.154 | 7.889 | 0.265 |
| MF EtOH | 3.812 | 0 | 26.224 | 23.594 | 2.63 | 3.746 | 0.002 | 26.298 | 0.002 | 0 | 0.002 |
| MF MEG | 0 | 0.009 | 2.573 | 0.017 | 2.556 | 0.006 | 0.023 | 0 | 2.49 | 0.006 | 2.483 |
| MF DEC | 0 | 0 | 6.253 | 3.96 | 2.294 | 2.294 | 4.871 | 1.353 | 0 | 0 | 0 |
| MF heavies | 0 | 0.007 | 4.778 | 0 | 4.778 | 0 | 0 | 0 | 1.581 | 1.581 | 0 |

From Tables 2 and 4 it appears that in the Example, the pressure at the top of distillation column 10 (2 bar) is lower than the pressure at the top of distillation column 5 (3 bar). On the other hand, in the Comparative Example, the pressure at the top of distillation column 8 (1 bar) is higher than the pressure at the top of distillation column 5 (0.12 bar).

In the Comparative Example, 20.9 kJ/g of DEC produced is required for heating in reactor 2 and distillation columns 5, 8 and 11. In the Example exemplifying the present invention, advantageously only 10.3 kJ/g of DEC produced is required for heating in reactor 2 and distillation columns 5, 8, 10 and 14.

What is claimed is:

1. A process for the preparation of an alkanediol and a dialkyl carbonate comprising:
   (a) reacting an alkylene carbonate and an alkanol in the presence of a transesterification catalyst to obtain a reaction mixture comprising dialkyl carbonate, unconverted alkanol, alkanediol and unconverted alkylene carbonate;
   (b) subjecting the reaction mixture to distillation in a first distillation column to obtain a top stream comprising dialkyl carbonate and alkanol and a bottom stream comprising dialkyl carbonate, alkanol, alkanediol and alkylene carbonate;
   (c) subjecting the bottom stream from the first distillation column to distillation in a second distillation column to obtain a top stream comprising dialkyl carbonate and alkanol and a bottom stream comprising alkanediol and alkylene carbonate;
   (d) recovering alkanediol from the bottom stream from the second distillation column; and
   (e) subjecting the top streams from the first and second distillation columns to distillation in a third distillation column to obtain a top stream comprising alkanol and a bottom stream comprising dialkyl carbonate.

2. A process according to claim 1, wherein a pressure at the top of the first distillation column is of from 0.5 to 10 bar.

3. A process according to claim 1, wherein a pressure at the top of the second distillation column is of from 10 mbar to 3 bar.

4. A process according to claim 3, wherein the pressure at the top of the second distillation column is lower than the pressure at the top of the first distillation column, and is of from 50 to 500 mbar.

5. A process according to claim 1, wherein a pressure at the top of the third distillation column is lower than the pressure at the top of the first distillation column.

6. A process according to claim 5, wherein the pressure at the top of the third distillation column is of from 0.1 to 5 bar.

7. A process according to claim 1, wherein a temperature at the bottom of the first, second and third distillation columns is of from 100 to 200 ° C.

8. A process according to claim 1, which is carried out continuously.

9. A process according to claim 1, wherein the transesterification catalyst is a heterogeneous catalyst.

10. A process according to claim 1, wherein the alkylene carbonate is ethylene carbonate or propylene carbonate and the alkanol is ethanol.

* * * * *